(12) United States Patent
Sjong

(10) Patent No.: US 9,835,605 B2
(45) Date of Patent: Dec. 5, 2017

(54) HYDROFLUOROCARBON DETECTION DEVICE

(71) Applicant: Empire Technology Development LLC, Wilmington, DE (US)

(72) Inventor: Angele Sjong, Louisville, CO (US)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 115 days.

(21) Appl. No.: 14/657,902

(22) Filed: Mar. 13, 2015

(65) Prior Publication Data

US 2015/0185193 A1    Jul. 2, 2015

Related U.S. Application Data

(62) Division of application No. 13/126,085, filed as application No. PCT/US2010/046984 on Aug. 27, 2010, now Pat. No. 8,993,338.

(51) Int. Cl.
*G01N 15/06* (2006.01)
*G01N 33/00* (2006.01)
*G01N 33/48* (2006.01)
*F25B 49/00* (2006.01)

(52) U.S. Cl.
CPC ....... *G01N 33/0049* (2013.01); *F25B 49/005* (2013.01); *F25B 2700/00* (2013.01); *Y10T 436/11* (2015.01); *Y10T 436/19* (2015.01); *Y10T 436/196666* (2015.01)

(58) Field of Classification Search
CPC ......... G01N 15/06; G01N 33/00; G01N 33/48
USPC ............. 422/83, 98; 436/43, 124, 126
See application file for complete search history.

(56) References Cited

U.S. PATENT DOCUMENTS

| | | | |
|---|---|---|---|
| 3,249,246 A | 5/1966 | Mahoney | |
| 3,926,560 A | 12/1975 | Gentry | |
| 5,104,513 A | 4/1992 | Lee et al. | |
| 5,293,130 A | 3/1994 | Allman et al. | |
| 8,418,530 B1* | 4/2013 | Scaringe et al. | 73/40.7 |
| 2005/0211949 A1* | 9/2005 | Bivens et al. | 252/67 |

(Continued)

FOREIGN PATENT DOCUMENTS

| | | |
|---|---|---|
| JP | 61-119758 U | 6/1986 |
| JP | 06-501777 T | 2/1994 |

(Continued)

OTHER PUBLICATIONS

"Refrigerant gas leak measurement," Ion Science Limited, Feb. 1, 2007, printed on Apr. 25, 2012 from http://www.qlimited.com/pdf/IonScience-GASr2pc-Q.pdf, 2 pages.

(Continued)

*Primary Examiner* — Brian J Sines
(74) *Attorney, Agent, or Firm* — Maschoff Brennan

(57) ABSTRACT

The present technology provides an illustrative hydrofluorocarbon (HFC) detection device that includes a decomposition component, a charged particle filter, and a sensing component. The decomposition component is configured to irradiate a gas sample with a radioactive element to decompose HFC gas under conditions sufficient to form hydrogen fluoride (HF) gas and one or more ionized particles. The charged particle filter is configured to filter the one or more ionized particles, and the sensing component is configured to detect the HF gas.

17 Claims, 6 Drawing Sheets

(56) References Cited

U.S. PATENT DOCUMENTS

| | | | |
|---|---|---|---|
| 2006/0249673 A1 | 11/2006 | Breach et al. | |
| 2011/0171743 A1 | 7/2011 | Baker et al. | |
| 2012/0052586 A1* | 3/2012 | Sjong | 436/126 |
| 2013/0230929 A1 | 9/2013 | Nakamura et al. | |

FOREIGN PATENT DOCUMENTS

| | | |
|---|---|---|
| JP | 2002-062278 A | 2/2002 |
| JP | 2007-504633 T | 3/2007 |
| JP | 2009-268962 | 11/2009 |
| WO | WO-93/08465 | 4/1993 |
| WO | WO-00/25104 | 5/2000 |
| WO | WO-2005/049759 | 6/2005 |

OTHER PUBLICATIONS

Chu, C. et al., "Radiation-induced hydrogen fluoride formation in fluorine-containing ethanes and ethenes," International Journal of Chemical Kinetics, Sep. 1976, vol. 8, pp. 753-764.
Honeywell webpage, "MDA Scientific Model IR-148," Honeywell Analytics, Inc., 2008., retrieved from the internet: <URL: http://www.honeywellanalytics.com/Technical%20Library/Americas/Model%20IR-148%20Relay%20Module/Datasheet/Model%20IR-148%20Relay%20Module.pdf>, 4 pages.
International Search Report and Written Opinion for PCT/US2010/046984 dated Oct. 6, 2010, 7 pages.
Moritz, W., et al., "Field-effect sensor for the selective detection of fluorocarbons," *Journal of Fluorine Chemistry*, 1999, vol. 93, pp. 61-67.
Moritz, W., et al., "Semiconductor sensors for the detection of fluorocarbons, fluorine and hydrogen fluoride," *Analytica Chimica Acta*, 1999, vol. 393, pp. 49-57.
Moritz, W., et al., "Silicon carbide based semiconductor sensor for the detection of fluorocarbons," *Sensors and Actuators B*, 1999, vol. 58, pp. 486-490.
Notice of Allowance in U.S. Appl. No. 13/126,085, dated Nov. 25, 2014 (9 pages).
Samon website, "HFC—Detectors with relay output," retrieved from the internet on Apr. 4, 2011: <URL: http://www.samon.se/res/PDF_eng/PB/PB-Eng-HFC001-0711.pdf>, 2 pages.
Sanchez, J.-B. et al., "Tin dioxide-based gas sensors for detection of hydrogen fluoride in air," Thin Solid Films, 2003, vol. 436, pp. 132-136.
Sierra Monitor Corporation website, "Model 4101-26 Hydrogen Fluoride Gas Sensor Module 4-20 mA," Instruction Manual, Mar. 1997, retrieved from the internet:<URL: http://www.sierramonitor.com/docs/pdf/Model_4101-26.pdf>, 17 pages.
Takateru Enomoto, et al., "Development of an Analytical Method for Atmospheric Halocarbons and Its Application to Airborne Observation," Journal of Atmospheric Environment, vol. 40 No. 1, p. 1-8, 2005.
Wikipedia website, "Americium," printed Feb. 2, 2011, retrieved from the internet: <URL: http://en.wikipedia.org/wiki/Americium>, 17 pages.

* cited by examiner

HYDROFLUOROCARBON DETECTION DEVICE

CROSS-REFERENCE TO RELATED APPLICATIONS

The present application is a divisional application of U.S. application Ser. No. 13/126,085, filed on Apr. 26, 2011, which is a U.S. national stage application under 35 U.S.C. §371 of International Application No. PCT/US2010/046984, filed on Aug. 27, 2010, of which the entire contents of each are incorporated herein by reference in their entirety.

BACKGROUND

The following description is provided to assist the understanding of the reader. None of the information provided or references cited is admitted to be prior art.

Hydrofluorocarbons (HFCs) are commonly used as refrigerants in household refrigeration devices such as refrigerators and air conditioners. HFCs are generally safe, inexpensive, chemically stable, efficient, non-toxic, and non-ozone depleting. However, many HFCs have high global warming potential (GWP) values. Gases having high GWP values are generally considered to increase global warming at a higher rate than gases having low GWP values. Due to the numerous advantages of HFCs, a suitable alternative refrigerant having similar safety, toxicity, and chemical stability characteristics is not readily available.

Many refrigeration devices currently in use are susceptible to HFC leaks. Such leaks enable the release of HFCs into the atmosphere thus further contributing to global warming. Consequently, there is a need for devices and systems that detect and prevent HFC emissions in the event of such a leak.

SUMMARY

The present technology provides an illustrative method for detecting hydrofluorocarbon (HFC) gas. The method includes irradiating a gas sample with a radioactive element under conditions sufficient to decompose HFC gas to form hydrogen fluoride (HF) gas and one or more ionized particles. The method further includes filtering the one or more ionized particles using a charged particle filter, and detecting the HF gas using an HF sensor, wherein the presence of the HF gas is indicative of the presence of HFC gas.

The present technology also provides an illustrative hydrofluorocarbon detection device that includes a decomposition component, a charged particle filter, and a sensing component. The decomposition component is configured to irradiate a gas sample with a radioactive element to decompose HFC gas under conditions sufficient to form hydrogen fluoride (HF) gas and one or more ionized particles. The charged particle filter is configured to filter the one or more ionized particles, and the sensing component is configured to detect the HF gas.

The present technology also includes an illustrative refrigerating device that includes a hydrofluorocarbon (HFC) detector that is configured to detect an HFC gas. The HFC detector includes a decomposition component, a charged particle filter, and a sensing component. The decomposition component is configured to irradiate an HFC gas sample with americium under conditions sufficient to decompose HFC gas to a composition including hydrogen fluoride (HF) gas and one or more ionized particles. The charged particle filter is configured to filter the one or more ionized particles, and the sensing component is configured to detect the HF gas.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings:

DETAILED DESCRIPTION

Figure 1:
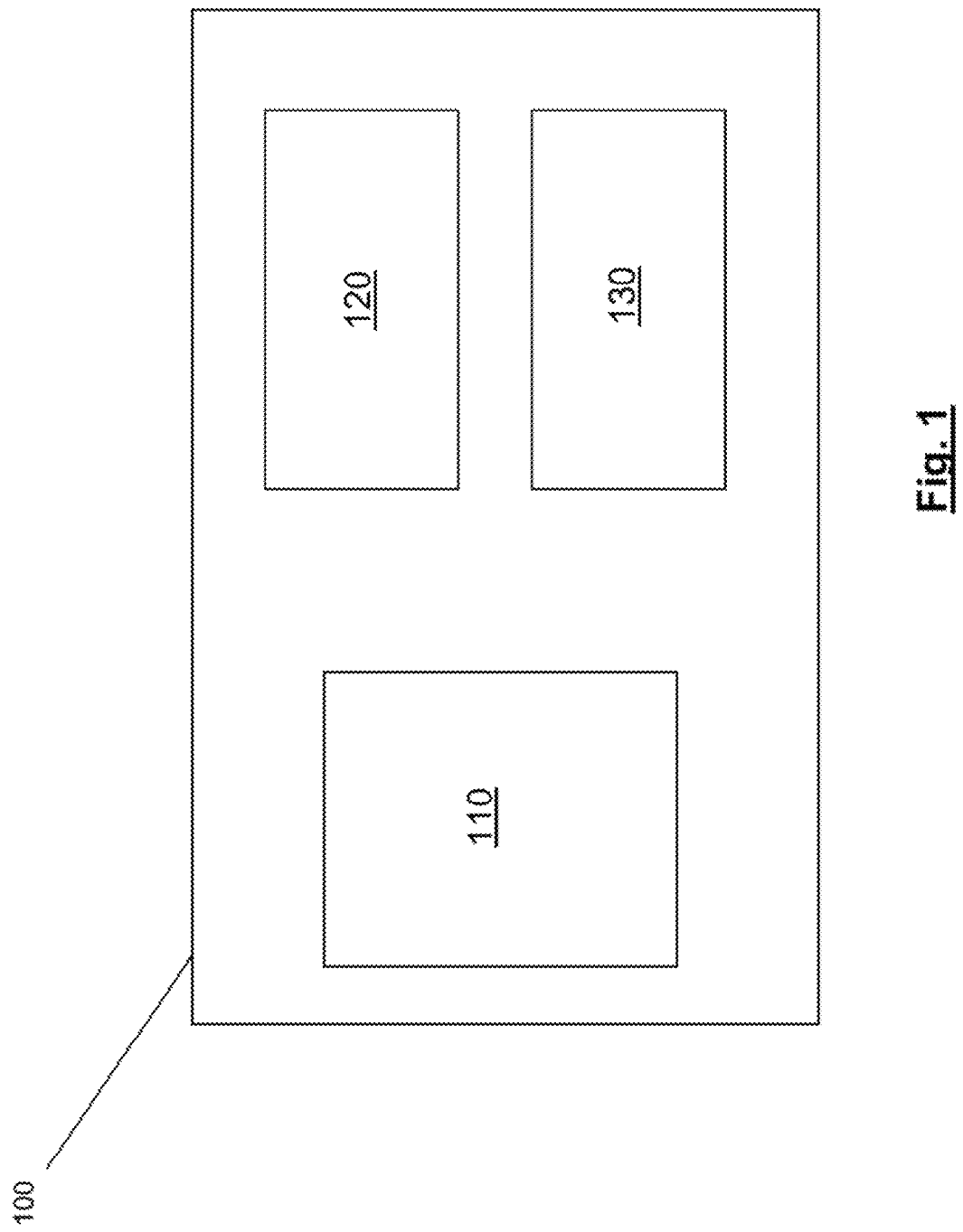
FIG. 1 depicts a hydrofluorocarbon (HFC) detection device in accordance with an illustrative embodiment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

Hydrofluorocarbon (HFC) leaks may occur in any type of refrigeration device (e.g., refrigerators, air conditioners, etc.) that utilizes HFCs as a refrigerant. HFCs have high global warming potential values and, as such, emission of HFCs into the atmosphere may contribute to global warming. Traditional HFC detectors are generally only able to detect large concentrations of HFC gas, e.g., detection in the range of 50 parts-per-million (ppm) or worse. In addition, traditional HFC detectors are generally expensive and bulky.

Described herein are illustrative devices and systems for detecting ambient, gaseous HFC compositions in much smaller concentrations. Such detection devices and systems may allow for detection of HFC compositions in the range of 10 parts-per-trillion (ppt). These HFC detection devices include a decomposition component that is configured to decompose a sample of HFC gas by irradiating the sample with an ionizing radiation. The irradiation of the sample of HFC gas causes the HFC gas to form hydrogen fluoride (HF) and one or more ionized particles. The HFC detection device further includes a charged particle filter that is configured to filter the one or more ionized particles and a sensing component that is configured to detect the HF gas. The presence of the HF gas (as detected by the sensing component) is indicative of the presence of HFC gas. The HFC detection device and method described below allow for detection of trace amounts of ambient HFC compositions in a safe, cost effective, and efficient manner.

FIG. 1 depicts a hydrofluorocarbon (HFC) detection device 100 in accordance with an illustrative embodiment. HFC detection device 100 includes a decomposition component 110, a charged particle filter 120, and a sensing component 130. Decomposition component 110 includes a compound selected to emit ionizing radiation which is used to decompose a sample of HFC gas. Air which may or may not include HFC gas may be distributed to decomposition component 110 via a fan or pump. In an alternative embodiment, decomposition component 110 may include a volume open to the flow of ambient air. According to such an embodiment, no specialized equipment is needed to move air into decomposition component 110. Accordingly, air is distributed to within a vicinity of the ionizing radiation produced by the selected compound as known to those of skill in the art and as are commonly used in household smoke detectors.

In an illustrative embodiment, the compound selected to emit ionizing radiation is an alpha emitting radioactive element such as 241-americium. In alternative embodiments, the compound may comprise any low-energy alpha-emitting radioactive element capable of decomposing HFC gas via ionizing radiation as known to those of skill in the art. In an example embodiment, 0.28 micrograms (μg) of 241-americium is used, although larger or small amounts of americium may be used. In an embodiment, the americium is enclosed within a container that includes a pinhole that allows the ionizing radiation from the 241-americium to escape and irradiate the ambient air collected in decomposition component 110. In an embodiment, the pinhole has a circular configuration with a diameter of 0.5-4 mm. In alternative embodiments, the pinhole may have any configuration known to those of skill in the art in accordance with design needs. In alternative embodiments, a low-energy gamma emitter such as 137-cesium may be used. Decomposition component 110 is configured to irradiate the sample of HFC gas, thus causing the decomposition of the HFC gas into hydrogen fluoride. In an illustrative embodiment, the sample of HFC gas is mixed with oxygen and nitrogen from the ambient air. As a result, the decomposition of the sample of HFC gas by irradiation will also result in the irradiation of the oxygen, nitrogen, and any other particles within the ambient air. The irradiation will thus produce not only hydrogen fluoride but also ionized oxygen, ionized nitrogen, and other ionized particles such as trace amounts of argon, carbon dioxide, methane, ozone, water vapor, etc.

Charged particle filter 120 is configured to filter the various ionized particles produced by the irradiation so as to prevent sensing component 130 from sensing the presence of these particles. Without the filtration of the various ionized particles by charged particle filter 120, the various ionized particles would cause the sensing component 130 to read a large noise signal, thus obscuring readings of hydrogen fluoride. In an illustrative embodiment, charged particle filter 120 includes a charged metal grid or mesh that is positioned between the area of HFC detection device 100 where the sample of HFC gas is decomposed and sensing component 130. In alternative embodiments, charged particle filter 120 may comprise a grid having a helical configuration.

In an embodiment, charged particle filter 120 may have a size of less than 1 $cm^3$ and may have openings having a diameter of approximately 50 μm. In some embodiments, charged particle filter 120 and sensing component 130 may be located within an inch of decomposition component 110. Sensing component 130 may be positioned within 0.5-5 mm of charged particle filter 120. In alternative embodiments, alternative spacing may be utilized in accordance with design needs.

Charged particle filter 120 allows neutral compounds such as hydrogen fluoride to pass through. However, the charged metal grid either repels or attracts the ionized particles, thus preventing their passage to sensing component 130. Charged particle filter 120 may be made of any material capable of repelling and attracting such ionized particles. For example, charged particle filter 120 may comprise tungsten, rhenium, tantalum, platinum, copper, or other similar materials known to those of skill in the art. In this way, the noise signal generated by the ionized particles at sensing component 130 is greatly reduced.

Sensing component 130 is configured to detect the presence of the hydrogen fluoride gas that is produced by the decomposition of the HFC gas. The detection of hydrogen fluoride gas by sensing component 130 is indicative of the presence of HFC gas. In an illustrative embodiment, sensing component 130 is a tin dioxide-based thin film sensor. Tin dioxide-based thin film sensors are capable of detecting the presence of very small amounts of hydrogen fluoride, e.g., around 50 ppb. Various other hydrogen fluoride detectors such as the semiconductor-based "WS-CRDS" hydrogen fluoride detector manufactured by Picarro may detect hydrogen fluoride concentrations down to around 10 ppt. In various embodiments, sensing component 130 may be any hydrogen fluoride detector known to those of skill in the art, e.g., semiconductor-based sensor, infrared sensor, etc. Various other hydrogen fluoride detectors such as the "WS-CRDS" hydrogen fluoride detector manufactured by Picarro may detect hydrogen fluoride concentrations down to around 10 ppt.

Figure 2:
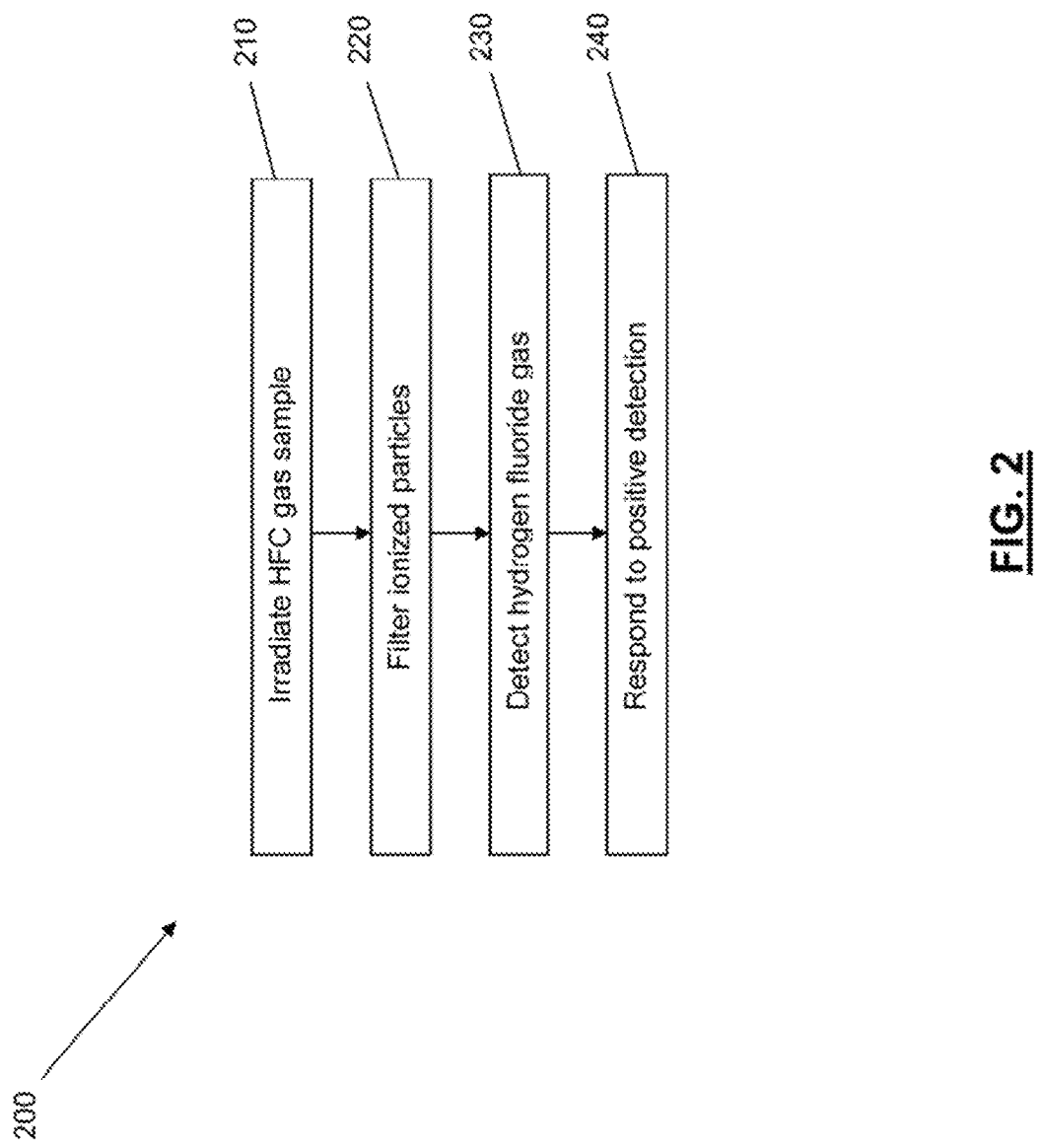
FIG. 2 depicts a method for detecting HFCs using the HFC detection device of FIG. 1 in accordance with an illustrative embodiment.

FIG. 2 depicts a method 200 for detecting an ambient HFC composition using HFC detection device 100 of FIG. 1 in accordance with an illustrative embodiment. In an operation 210, HFC detection device 100 irradiates a sample of HFC gas with an ionizing radiation via a decomposition component. In an embodiment, $2.4 \times 10^{18}$ eV/gh of 241-americium may be used to irradiate the sample of HFC gas. In alternative embodiments, varying concentrations of 241-americium may be used in accordance with design needs. In alternative embodiments, the HFC gas may be irradiated with a gamma emitter, such as but not limited to 137-cesium or any other radioactive element capable of decomposing HFC gas via ionizing radiation as known to those of skill in the art. The irradiation of the sample of HFC gas causes the HFC gas to decompose into hydrogen fluoride gas and one or more ionized particles. In an illustrative embodiment, the sample of HFC gas may be mixed with or present in ambient air that may include oxygen, nitrogen, and various other particles. As a result the irradiation of the sample of HFC gas will also result in the irradiation of other particles in the ambient air included in the sample of HFC gas to produce hydrogen fluoride (from the decomposition of the HFC gas)

as well as ionized oxygen, nitrogen, and other particles (from the irradiation of the ambient air).

In an operation 220, a charged particle filter is used to filter the ionized particles. In an illustrative embodiment, a metal filter such as a mesh grid is charged. The charged metal grid allows neutral compounds such as hydrogen fluoride to pass through. The charged particle filter repels or attracts the various ionized particles (depending on the polarities of the ionized particles and the filter) to prevent the movement of ionized particles to an area near the sensing component. Without the filtration of the various ionized particles by the charged particle filter, the various ionized particles would likely cause a large noise signal in the sensing component, thus obscuring any readings of hydrogen fluoride.

In an operation 230, a sensing component such as a tin dioxide-based thin film sensor or other hydrogen fluoride detector known to those of skill in the art detects hydrogen fluoride that is produced by the decomposition of the sample of HFC gas. Detection of hydrogen fluoride gas is thus considered an indication of the presence of HFC gas. In an embodiment, the concentration of HFC gas within the air may be determined based on the concentration of hydrogen fluoride gas detected by the sensing component. The relationship of the concentration of detected hydrogen fluoride gas to HFC gas will depend on the type of HFC gas within the air, because different types of HFC gas will produce different amounts of hydrogen fluoride gas when irradiated. In an embodiment, the concentration of HFC gas within the air is determined by calculating the amount of HFC gas required to produce the amount of HF gas detected by the sensing component (and which results from the irradiation of the HFC gas with the irradiation compound). According to such an embodiment, the sensing component may include a microprocessor configured to perform such a calculation. Alternatively, the sensing component may be communicatively coupled to an external microprocessor that is configured to perform the calculation. In an embodiment, the type of HFC gas expected to be detected by the detection device is manually input (and/or pre-programmed) into the microprocessor to ensure that the correct calculations are used to determine the amount of HFC gas.

In an operation 240, an appropriate response to a positive or negative detection of hydrogen fluoride may be conducted. In an illustrative embodiment, in response to a positive detection of hydrogen fluoride, an alarm is triggered. As discussed above, the detection of hydrogen fluoride having a concentration of down to 10 ppt may be sufficient to trigger the alarm. However, the threshold amount required to trigger the alarm may be any amount that is capable of being detected by an HFC sensor. Accordingly, as more sensitive HFC sensors are developed, lower threshold amounts may be used to trigger the alarm.

The alarm may be any alarm known to those of skill in the art. For example, the alarm may be an audible alarm, a visual alarm, or a combination. In an embodiment, the sensing component may be communicatively coupled to a computer that is configured to provide the alarm. In alternative embodiments, the computer may be configured to provide a wireless output and a readout as known to those of skill in the art to communicate the positive detection of hydrogen fluoride. In an alternative embodiment, the computer may be configured to trigger an HFC elimination device in response to a positive detection of hydrogen fluoride in order to eliminate ambient HFC gas. The computer may communicate with the HFC elimination device via a hardwired or wireless connection as known to those of skill in the art. In response to a negative detection of hydrogen fluoride, the computer may be further configured to convey an appropriate signal (e.g., an audible or visual signal) indicating that no HFC gas or that an amount of HFC gas below a detectable amount is currently present in the air. For example, a readout may be presented on a display indicating the lack of HFC gas.

Figure 3:
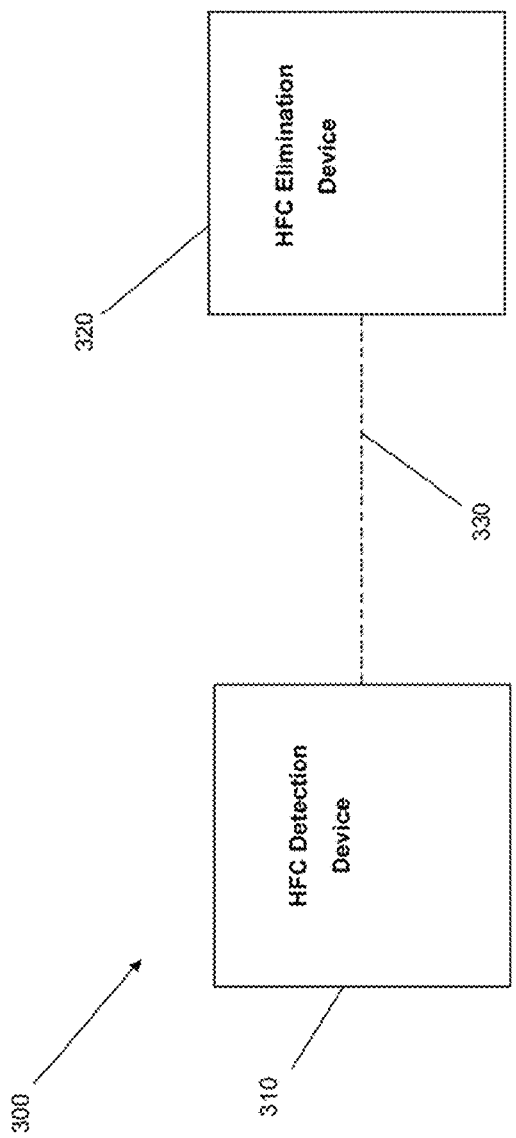
FIG. 3 depicts an HFC detection and elimination system in accordance with an illustrative embodiment.

FIG. 3 depicts an HFC detection and elimination system 300 in accordance with an illustrative embodiment. System 300 includes an HFC detection device 310 that is communicatively coupled to an HFC elimination device 320 by a communication channel 330. In an embodiment, HFC detection device 310 includes a decomposition component, a charged particle filter, and a sensing component as discussed above. The decomposition component is configured to irradiate ambient air with americium or any other radiation-emitting compound configured to produce ionizing radiation. If the ambient air includes an HFC composition, the irradiated americium causes the HFC composition to decompose to a composition which includes hydrogen fluoride gas and one or more ionized particles. The sensing component of HFC detection device 310 is configured to detect the presence of hydrogen fluoride gas. Consequently, the sensing component will detect the presence of any hydrogen fluoride gas that results from the decomposition of an HFC composition in the ambient air due to irradiation with americium. Upon sensing the hydrogen fluoride gas, HFC detection device 310 outputs an electrical signal indicating the presence of the HFC composition. The charged particle filter repels or attracts the one or more ionized particles thus preventing the movement of the one or more ionized particles from a location where the HFC composition is decomposed to the sensing component. As a result, the charged particle filter prevents the occurrence of excessive noise at the sensing component due to the sensing of the ionized particles.

HFC elimination device 320 may be any device known to those of skill in the art that is capable of eliminating ambient HFC gas. In an embodiment, HFC elimination device 320 includes an outer glass surface formed on an external case and an internal heating element positioned within the external case as described below with respect to FIGS. 4 and 5. In response to an electrical signal from HFC detection device 310, the internal heating element of HFC elimination device 320 is configured to heat the glass surface so that upon contact with an ambient HFC composition, the HFC composition will be decomposed as discussed further below.

Figure 4:
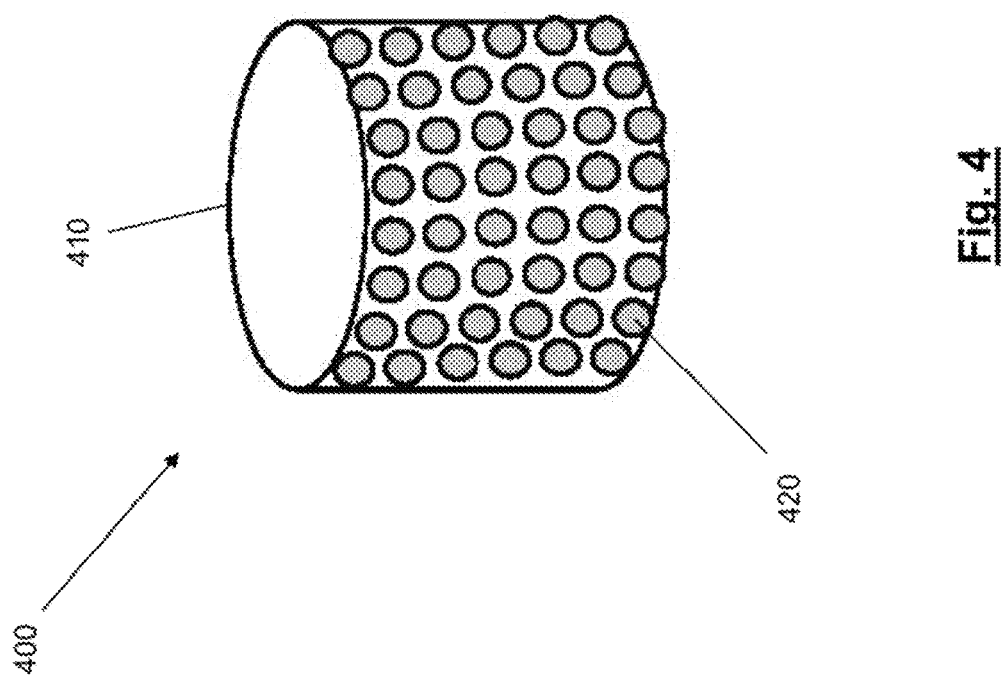
FIG. 4 depicts a hydrofluorocarbon (HFC) elimination device in accordance with an illustrative embodiment.
Figure 5:
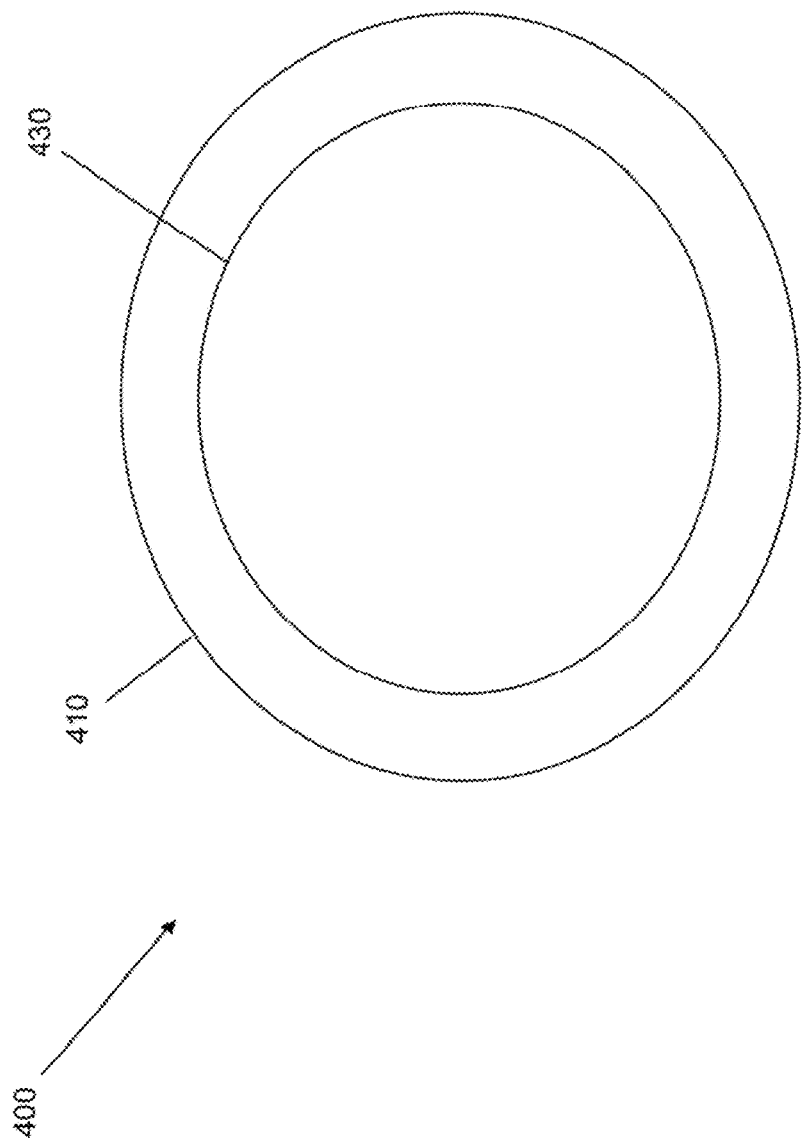
FIG. 5 depicts a cross-sectional view of the HFC elimination device of FIG. 4 in accordance with an illustrative embodiment.

FIG. 4 depicts a hydrofluorocarbon (HFC) elimination device 400 in accordance with an illustrative embodiment. HFC elimination device 400 includes a component 410 and a heating element 430 (not shown in FIG. 4). Heating element 430 may include an electric heating coil, an electric heating rod, or any other heating device known to those of skill in the art. In an embodiment, heating element 430 is positioned within component 410 as illustrated in FIG. 5. Component 410 may be formed of metal, glass, or any other products known to those of skill in the art that would allow for heat transfer between heating element 430 and a glass surface 420. Glass surface 420 is formed on the surface of component 410. Glass surface 420 may comprise 45S5 bioglass, soda lime glass, or any other glass known to those of skill in the art that is capable of reacting with HFCs as described below. Glass surface 420 may comprise one or more glass beads. In an embodiment, glass surface 420 comprises a plurality of glass beads. In another alternative embodiment, glass surface 420 may include a glass frit, i.e., a granulated composition of ceramic, sand, powder, etc. used to make glass. In various other embodiments, any glass configuration known to those of skill in the art that allows for contact between the heated glass and ambient air could be used.

FIG. 5 depicts a cross-sectional view of HFC elimination device 400 in accordance with an illustrative embodiment. As discussed above, HFC elimination device 400 includes a heating element 430 that is positioned within component 410. In alternative embodiments, heating element 430 need not be positioned within component 410 so long as heating element 430 is positioned within a proximity of component 410 such that it may sufficiently heat glass surface 420. For example, in an illustrative embodiment, component 410 may comprise a sheet of metal having a glass surface and heating element 430 may be positioned behind component 410 but in sufficient proximity to heat the glass surface.

In response to a signal from an HFC sensor indicating the presence of an ambient, gaseous HFC composition, heating element 430 heats glass surface 420. The HFC sensor may be a tin oxide based semiconductor sensor, an infrared sensor, or any other HFC sensor known to those of skill in the art. In an illustrative embodiment, the HFC sensor is connected to an analog or digital input of a microprocessor which is configured to control the heating element. In various embodiments, the HFC sensor may be connected to the microprocessor via a hardwired or wireless communication channel as known to those of skill in the art.

In an alternative embodiment, heating element 430 may be configured to periodically turn on and off. Glass surface 420 is heated via a radiant heating process, whereby heat emitted from heating element 430 radiates outward and is absorbed by glass surface 420. Upon contact with the ambient, gaseous HFC composition, heated glass surface 420 reacts with the HFC composition to form various non-toxic, untraceable byproducts that have smaller global warming potential values than the ambient, gaseous HFC composition.

Heated glass surface 420 reacts with the ambient, gaseous HFC composition through a dealkalization process in which alkali ions are pulled from glass surface 420 and react with the ambient, gaseous HFC composition. The alkali ions of glass surface 420 include sodium oxide ($Na_2O$) and calcium oxide (CaO). As the ambient, gaseous HFC composition reacts with the sodium oxide and calcium oxide of heated glass surface 420, the HFC composition is decomposed and non-toxic, untraceable levels of sodium fluoride and calcium fluoride are formed. In alternative embodiments, sodium chloride (NaCl) and calcium chloride ($CaCl_2$) may be produced. U.S. Pat. No. 3,249,246 to William P. Mahoney uses a similar chemical reaction to dealkalize soda lime glass container surfaces for food and drug applications, and is herein incorporated by reference in its entirety.

In an illustrative embodiment, system 300 is embodied as part of a refrigeration device such as a refrigerator or an air conditioning device. Such a refrigeration device may include a refrigerant coil through which a refrigerant that includes an HFC composition is passed. The refrigeration device may also include a compressor for compressing the refrigerant. HFC detection device 310 and/or HFC elimination device 320 may be located inside the refrigerant coil, within an area surrounded by the refrigerant coil, or in close proximity to the refrigerant coil of the refrigerant device. In an alternative embodiment, HFC detection device 310 and/or HFC elimination device 320 may be located in or near the compressor. In other embodiments, HFC detection device 310 and/or HFC elimination device 320 may be located in proximity to any component of a refrigeration device where a leak of an HFC composition may be possible as known to those of skill in the art.

Communication channel 330 may be any type of communication channel known to those of skill in the art configured in a manner such that HFC detection device 310 may communicate a signal to HFC elimination device 320. In an embodiment, HFC detection device 310 may be hardwired to HFC elimination device 320. In an alternative embodiment, communication channel 330 may be a wireless communication path. In accordance with such an embodiment, HFC detection device 310 also includes a wireless transmitter configured to transmit a signal from HFC detection device 310 to a wireless receiver of HFC elimination device 320.

Figure 6:
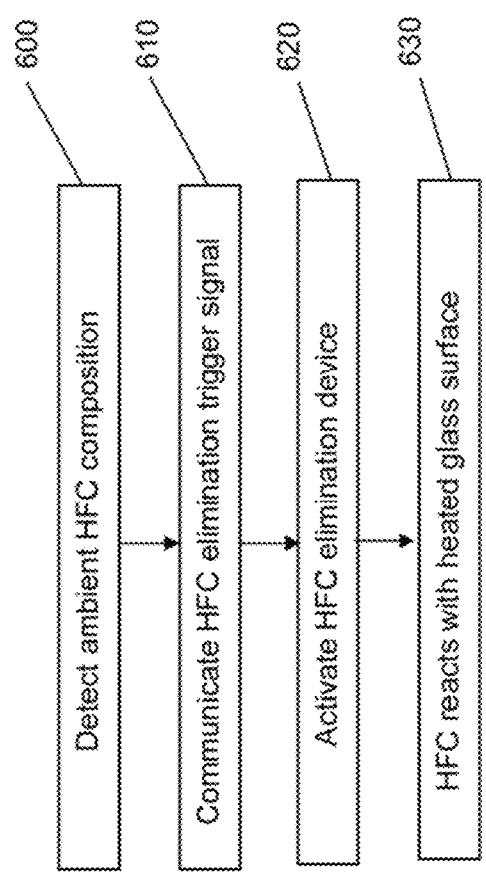
FIG. 6 depicts a method for detecting and eliminating HFCs using the HFC detection and elimination system of FIG. 3 in accordance with an illustrative embodiment.

FIG. 6 depicts a method for detecting and eliminating an ambient HFC composition using HFC detection and elimination system 300 of FIG. 3 in accordance with an illustrative embodiment. In an operation 600, an HFC detection device detects an ambient HFC composition. In response to detection of the ambient HFC composition, the HFC detection device communicates a trigger signal to an HFC elimination device in an operation 610, thereby indicating the presence of an ambient HFC composition. In an embodiment, the presence of the ambient HFC composition, may indicate a leak within a cooling system of a refrigeration device such as a refrigerator or an air conditioner. In an operation 620, in response to receiving the trigger signal, an HFC elimination device, as known to those of skill in the art, may be activated in order to eliminate the ambient HFC composition. In an illustrative embodiment, an internal heating element of the HFC elimination device heats a glass surface of the HFC elimination device to a temperature sufficient to cause decomposition of the ambient HFC composition upon contact with the heated glass surface. In one possible embodiment, the glass surface is heated to a temperature of between 200° C. and 250° C.

In an operation 630, the heated glass surface reacts with the ambient HFC composition through a dealkalization process in which alkali ions such as Na+ and Ca2+ from sodium oxide ($Na_2O$) and calcium oxide (CaO), respectively, are pulled from the glass surface and react with the ambient HFC composition. The glass surface may include high levels of sodium oxide ($Na_2O$) and calcium oxide (CaO). As the ambient HFC composition reacts with the sodium oxide and calcium oxide of the heated glass surface, the ambient HFC composition is decomposed and non-toxic, non-traceable levels of sodium fluoride and calcium fluoride are formed. In alternative embodiments, sodium chloride (NaCl) and calcium chloride ($CaCl_2$) may be produced from the reaction. In this way, the ambient HFC composition is decomposed to form non-toxic byproducts with lower global warming potential values than the ambient HFC composition.

In alternative embodiments, any HFC elimination device known to those of skill in the art may be used. Accordingly, operations 620 and 630 may be altered or canceled according to the particular embodiment used.

One or more flow diagrams may have been used herein. The use of flow diagrams is not meant to be limiting with respect to the order of operations performed. The herein described subject matter sometimes illustrates different components contained within, or connected with, different other components. It is to be understood that such depicted architectures are merely illustrative, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general, such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general, such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. A hydrofluorocarbon (HFC) detection device comprising:
a decomposition component configured to irradiate a gas sample with a radioactive element to decompose HFC gas under conditions sufficient to form hydrogen fluoride (HF) gas and one or more ionized particles;
a charged particle filter configured to filter the one or more ionized particles; and
a sensing component configured to detect the HF gas, wherein the charged particle filter is positioned between the decomposition component and the sensing component.

2. The HFC detection device of claim 1, further comprising a trigger component configured to trigger an alarm in response to detection of the HF gas.

3. The HFC detection device of claim 1, further comprising a trigger component configured to trigger an HFC elimination device in response to detection of the HF gas.

4. The HFC detection device of claim 1, wherein the HFC gas comprises at least one of tetrafluoroethane, pentafluoroethane, trifluoroethane, or difluoroethane.

5. The HFC detection device of claim 1, wherein the sensing component comprises a semiconductor gas sensor or a tin dioxide-based thin film sensor.

6. The HFC detection device of claim 1, wherein the radioactive element comprises an alpha-emitting compound.

7. The HFC detection device of claim 1, wherein the radioactive element comprises a gamma-emitting compound.

8. The HFC detection device of claim 1, wherein the charged particle filter comprises a charged metal grid.

9. The HFC detection device of claim 1, wherein the charged particle filter is configured to prevent the one or more ionized particles from moving from an area of the decomposition component to an area of the sensing component, and wherein the charged particle filter is configured to allow the HF gas to move from the area of the decomposition component to the area of the sensing component.

10. A refrigerating device comprising:
a hydrofluorocarbon (HFC) detector configured to detect an HFC gas, wherein the HFC detector comprises:
a decomposition component configured to irradiate an HFC gas sample with a radioactive element under conditions sufficient to decompose HFC gas to a composition including hydrogen fluoride (HF) gas and one or more ionized particles;
a charged particle filter configured to filter the one or more ionized particles; and a sensing component configured to detect the HF gas, wherein the charged particle filter is positioned between the decomposition component and the sensing component.

11. The refrigerating device of claim 10, further comprising an HFC elimination device configured to convert the HFC gas to an alternative composition.

12. The refrigerating device of claim 11, wherein the HFC detector further comprises a trigger component configured to activate the HFC elimination device in response to detection of the HF gas.

13. The refrigerating device of claim 11, wherein the alternative composition has a lesser global warming potential value than the HFC gas, and wherein the alternative composition comprises at least one of calcium fluoride or sodium fluoride.

14. The refrigerating device of claim 11, wherein the HFC elimination device comprises an external glass surface and a heating element located within the external glass surface.

15. The refrigerating device of claim 11, wherein the HFC elimination device is configured to convert the HFC gas to the alternative composition in response to a signal from the sensing component indicating that the sensing component detected the HF gas.

16. The refrigerating device of claim 10, wherein the HFC detector further comprises a trigger component configured to trigger an alarm in response to detection of the HF gas.

17. The refrigerating device of claim 10, further comprising a refrigerant coil and a compressor, and wherein the HFC detector is located within an area surrounded by the refrigerant coil or is located within the compressor.

* * * * *